United States Patent
Melder et al.

(10) Patent No.: US 12,078,691 B2
(45) Date of Patent: Sep. 3, 2024

(54) HOUSING ASSEMBLY FOR ACCOMMODATING PRINTED CIRCUIT BOARDS

(71) Applicant: Stryker European Operations Limited, Carrigtwohill (IE)

(72) Inventors: Ulrich Melder, Freiburg (DE); Janina Fritzenschaft, Freiburg (DE); Fabian Riegelsberger, Umkirch (DE); Hans Schoepp, Freiburg (DE)

(73) Assignee: Stryker European Operations Limited, Carrigtwohill (IE)

( * ) Notice: Subject to any disclaimer, the term of this patent is extended or adjusted under 35 U.S.C. 154(b) by 190 days.

(21) Appl. No.: 17/903,395

(22) Filed: Sep. 6, 2022

(65) Prior Publication Data

US 2023/0070115 A1 Mar. 9, 2023

(30) Foreign Application Priority Data

Sep. 9, 2021 (EP) .................................... 21195735

(51) Int. Cl.
*G01R 33/00* (2006.01)
*H05K 5/02* (2006.01)
*H05K 5/03* (2006.01)

(52) U.S. Cl.
CPC ....... *G01R 33/0047* (2013.01); *H05K 5/0213* (2013.01); *H05K 5/03* (2013.01)

(58) Field of Classification Search
CPC .... G01R 33/0047; H05K 5/0213; H05K 5/03; H05K 9/0037; H05K 5/0204;

(Continued)

(56) References Cited

U.S. PATENT DOCUMENTS

| 5,118,903 A | 6/1992 | Schupp et al. |
| 6,226,182 B1 | 5/2001 | Maehara |

(Continued)

FOREIGN PATENT DOCUMENTS

| CN | 102026505 B | 7/2015 |
| CN | 110083212 A | 8/2019 |

(Continued)

OTHER PUBLICATIONS

English language description for CN 305757047 extracted from espacenet.com database on Apr. 3, 2023, 1 page.

(Continued)

*Primary Examiner* — Giovanni Astacio-Oquendo
(74) *Attorney, Agent, or Firm* — Howard & Howard Attorneys PLLC

(57) ABSTRACT

The present disclosure relates to a housing assembly for accommodating printed circuit boards (PCBs). The housing assembly comprises a first housing portion configured to accommodate a first PCB, a second housing portion configured to accommodate a second PCB, and a separating portion for separating the first housing portion from the second housing portion. The separating portion comprises a first separating region in which the first housing portion and the second housing portion overlap and a second separating region that extends beyond the second housing portion and covers the first housing portion. The second separating region comprises one or more convection openings.

20 Claims, 9 Drawing Sheets

(58) Field of Classification Search
CPC ............ H05K 7/20418; H05K 9/0049; H05K 7/20127; A61B 5/062; A61B 2034/2051; A61B 34/20
USPC ...................................... 324/156, 76.11, 200
See application file for complete search history.

(56) References Cited

U.S. PATENT DOCUMENTS

| | | | |
|---|---|---|---|
| 7,254,035 | B2 | 8/2007 | Sasaki et al. |
| D560,528 | S | 1/2008 | Chen |
| D600,149 | S | 9/2009 | Chen |
| 7,903,405 | B1 | 3/2011 | Miller et al. |
| D669,799 | S | 10/2012 | Okudaira et al. |
| D724,963 | S | 3/2015 | Ambrose |
| D755,653 | S | 5/2016 | Shinmei et al. |
| D805,932 | S | 12/2017 | Koeniger et al. |
| 10,206,316 | B1 * | 2/2019 | Koch ........................ H05K 5/04 |
| D865,549 | S | 11/2019 | Gaucher et al. |
| D883,114 | S | 5/2020 | Nordahl et al. |
| 10,791,634 | B2 | 9/2020 | Inoue et al. |
| 11,013,129 | B2 | 5/2021 | Inoue et al. |
| 11,019,736 | B2 | 5/2021 | Woo et al. |
| 11,152,664 | B2 | 10/2021 | Reykhert |
| 11,189,906 | B2 | 11/2021 | Park |
| D942,935 | S | 2/2022 | Wang |
| 11,627,654 | B2 | 4/2023 | Jung |
| 2002/0089825 | A1 | 7/2002 | Sasaki et al. |
| 2004/0212961 | A1 | 10/2004 | Harris |
| 2007/0295904 | A1 | 12/2007 | Antanouski |
| 2011/0069449 | A1 | 3/2011 | Miller et al. |
| 2015/0109745 | A1 | 4/2015 | Nagai et al. |
| 2015/0247933 | A1 | 9/2015 | McQuirter et al. |
| 2016/0252325 | A1 | 9/2016 | Sammut et al. |
| 2017/0238430 | A1 | 8/2017 | Moon |
| 2020/0137926 | A1 * | 4/2020 | Wöhlte ............... H05K 7/20436 |
| 2021/0392736 | A1 | 12/2021 | Koo et al. |
| 2021/0410268 | A1 | 12/2021 | Moon et al. |
| 2022/0013964 | A1 * | 1/2022 | Meghpara ............. H02K 11/33 |
| 2022/0151106 | A1 | 5/2022 | Kang et al. |
| 2022/0179106 | A1 | 6/2022 | Gendotti et al. |
| 2022/0210905 | A1 | 6/2022 | Choi et al. |
| 2022/0400575 | A1 | 12/2022 | Uhm et al. |

FOREIGN PATENT DOCUMENTS

| | | |
|---|---|---|
| CN | 305757047 | 5/2020 |
| CN | 306358263 | 3/2021 |
| CN | 306784997 | 8/2021 |
| CN | 307017475 | 12/2021 |
| CN | 307697083 | 11/2022 |
| DE | 7632332 U1 | 1/1977 |
| DE | 3506798 A1 | 8/1986 |
| DE | 3933123 A1 | 4/1991 |
| DE | 60017826 T2 | 6/2005 |
| DE | 202011000282 U1 | 1/2012 |
| DE | 102014220489 A1 | 4/2016 |
| DE | 102017201582 A1 | 8/2018 |
| EP | 2983460 A1 | 2/2016 |
| EP | 3399225 A1 | 11/2018 |
| GB | 6237035 | 11/2022 |
| JP | H1117372 A | 1/1999 |
| RU | 00085468 | 6/2013 |

OTHER PUBLICATIONS

English language description for CN 306358263 extracted from espacenet.com database on Apr. 3, 2023, 1 page.
English language description for CN 306784997 extracted from espacenet.com database on Apr. 3, 2023, 1 page.
English language description for CN 307017475 extracted from espacenet.com database on Apr. 3, 2023, 1 page.
English language description for CN 307697083 extracted from espacenet.com database on Apr. 3, 2023, 1 page.
English language description for RU 00085468 extracted from espacenet.com database on Apr. 3, 2023, 1 page.
amazon,com, "Attposn EMF Meters Reader Ghost Hunting, Geiger Counter, Digital Handheld EMF Detector Electromagnetic Field Radiation Detector", 2022, 11 pages.
amazon.com, "Color Tree Handheld LED EMF Magnetic Filed Ghost Hunting Detector Electromagnetic Paranormal Equipment Tester 50Hz-20,000Hz Black", 2020, 11 pages.
amazon.com , "LATINEX AF-3500 EMF Meter Reader Detector and Reader With Calibration Certificate—Measures RF and Microwaves, 3-Axis Guass Magnetic Fields and Electrical Fileds ELF", 2019, 16 pages.
English language abstract for CN 102026505 B extracted from espacenet.com database on Sep. 7, 2022, 1 page.
English language abstract for CN 110083212 A extracted from espacenet.com database on Sep. 7, 2022, 1 page.
English language abstract and machine-assisted English translation for DE 76 32 332 U extracted from espacenet.com database on Sep. 7, 2022, 7 pages.
Machine-assisted English language abstract and machine-assisted English translation for DE 10 2014 220 489 A1 extracted from espacenet.com database on Sep. 7, 2022, 11 pages.
English language abstract and machine-assisted English translation for DE 35 06 798 A1 extracted from espacenet.com database on Sep. 7, 2022, 7 pages.
English language abstract for DE 39 33 123 A1 extracted from espacenet.com database on Sep. 7, 2022, 1 page.
English language abstract for DE 600 17 826 T2 extracted from espacenet.com database on Sep. 7, 2022, 2 pages.
Machine-assisted English language abstract and machine-assisted English translation for DE 20 2011 000 282 U1 extracted from espacenet.com database on Sep. 7, 2022, 10 pages.
Machine-assisted English language abstract and machine-assisted English translation for DE 10 2017 201 582 A1 extracted from espacenet.com database on Sep. 7, 2022, 14 pages.
Machine-assisted English language abstract and machine-assisted English translation for EP 3 399 225 A1 extracted from espacenet.com database on Sep. 7, 2022, 17 pages.
English language abstract and machine-assisted English translation for JPH 11-17372 A extracted from espacenet.com database on Sep. 7, 2022, 8 pages.

* cited by examiner

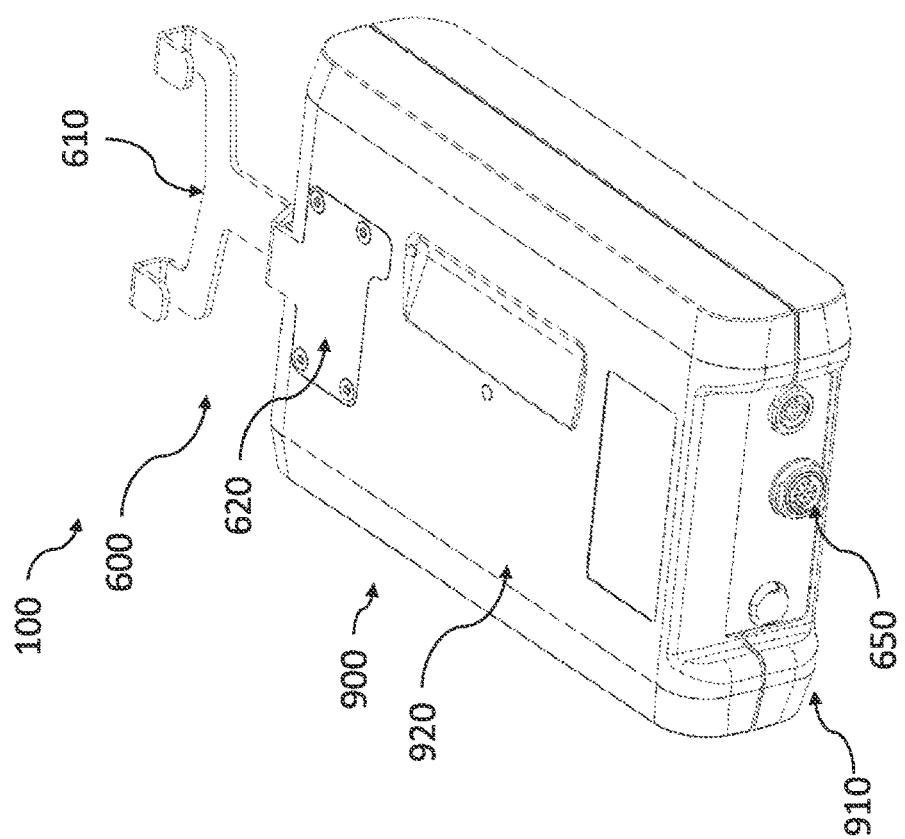
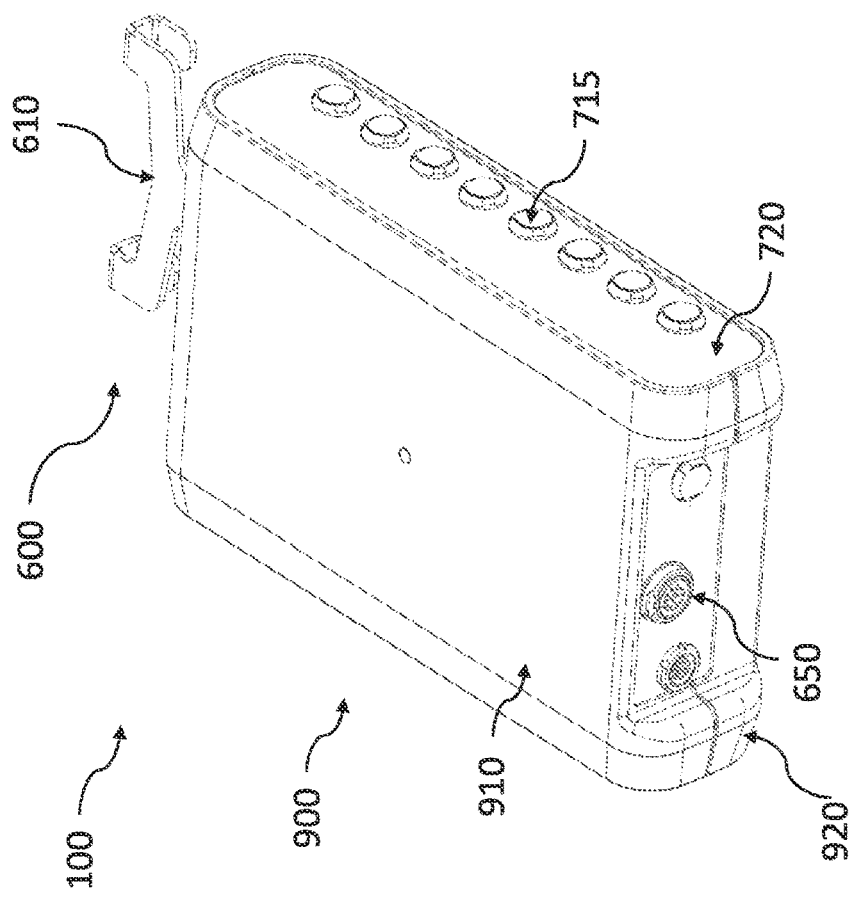

US 12,078,691 B2

HOUSING ASSEMBLY FOR ACCOMMODATING PRINTED CIRCUIT BOARDS

PRIORITY CLAIM

This application claims priority under 35 U.S.C. § 119 to European Patent Application No. 21195735.2, filed Sep. 9, 2021, the entire contents of which are hereby incorporated by reference.

TECHNICAL FIELD

The present disclosure relates generally to the field of housings for electronic components. The disclosure relates in particular to a housing assembly for accommodating printed circuit boards. The housing assembly may be part of an electromagnetic tracking system.

BACKGROUND

Most electronic devices include heat-generating electronic components mounted on a printed circuit board (PCB). Such electronic components include MOSFETs, diodes, drivers, processors, etc. Accordingly, when the electronic device is in operation, there is a risk of the electronic components generating excessive heat. If the excessive heat cannot be effectively transferred to the environment or dissipated otherwise, the excessive heat, in particular a locally elevated temperature, can result in the failure of the electronic components. Further, most approaches for increasing the performance of electronic devices or downsizing the electronic devices result in an increased component density on the PCB, which also contributes to thermal problems. Thus, various heat dissipation approaches have been developed.

In general, such heat dissipation approaches are categorized in active and passive heat dissipation. In the prior art, one example of active heat dissipation is to utilize fans to create an airflow for transporting warm air away from the heat-generating electronic components or cold air to the heat-generating electronic components (see, e.g., DE 20 2011 000 282 U1). Passive heat dissipation approaches may rely on convection (see, e.g., DE 76 32 332 U) or on conduction, e.g., utilizing heat conducting elements connected to a heat sink (see, e.g., DE 10 2014 220 489 A1).

For electronic devices used in electromagnetic tracking (e.g., in a surgical environment), not only an efficient heat dissipation is required, but also possible interferences due to magnetic or electromagnetic fields acting on the electronic components have to be taken into account. Interferences may be caused for example by the electronic components of the electronic devices themselves or by electromagnetic fields generated by external electrical devices, e.g., field generators.

Unwanted interferences may influence and possibly falsify signals that are generated by, transmitted to or received from electrical components of the electronic device. In a surgical environment, the falsified signals generated during electromagnetic tracking may lead to personal injuries, e.g., due to an incorrect determination of a position of a surgical instrument. Evidently, such injuries can also occur in case excessive heat leads to failure of electronic components when the electronic device is used during a surgical procedure.

SUMMARY

Accordingly, an object of the present invention is to provide a housing assembly for accommodating multiple printed circuit boards and efficiently addressing at least heat-related problems, optionally in combination with solving one or more further problems, such as providing an efficient electromagnetic shielding.

According to an aspect of the present disclosure, there is provided a housing assembly for accommodating printed circuit boards, PCBs. The housing assembly comprises a first housing portion configured to accommodate a first PCB, a second housing portion configured to accommodate a second PCB, and a separating portion for separating the first housing portion from the second housing portion. The separating portion comprises a first region in which the first housing portion and the second housing portion overlap and a second region that extends beyond the second housing portion and covers the first housing portion. The second region comprises one or more first convection openings.

In one variant, at least the first PCB may comprise one or more heat-generating electrical components. The one or more heat-generating electrical components of the first PCB may also themselves generate electromagnetic fields during operation.

The first PCB may be accommodated in the first housing portion with the one or more heat-generating electrical components being located adjacent to the first convection openings. The first PCB may be a commercially available PCB, e.g., a "NDI Aurora" system control unit (SCU) in a PCB format configured for integration into original equipment manufacturer (OEM) carts, as sold by Northern Digital Inc.

The one or more heat generating components may be located in a first area of the first PCB, e.g., adjacent to each other, so that a major part of the excess heat generation of the first PCB takes place locally, i.e., at the first area of the first PCB. The first area of the first PCB may be arranged adjacent to the first convection openings. The one or more first convection openings may be inlet openings configured for allowing an airflow from outside the first housing portion into an interior of the first housing portion.

The second PCB may comprise one or more electric ports configured to be coupled to one or more external electromagnetic field sensors. Moreover, the second PCB may comprise one or more signal processing components configured to process sensors signals generated by the one or more electromagnetic field sensors. The second PCB may be a commercially available PCB, e.g., a "NDI Aurora" sensor interface unit (SIU) in a PCB format, as sold by Northern Digital Inc.

In one variant, the one or more heat-generating electrical components on the first PCB may be drivers for controlling an external electromagnetic field generator that generates an electrical field to be measured by the one or more external electromagnetic field sensors. In certain implementations, the one or more heat-generating components, especially when also capable of generating interfering electromagnetic fields, are located (e.g., only), or concentrated, adjacent the second separating portion and, thus, may be spaced apart from the first separating portion where the first housing portion and the second housing portion (the latter possibly with the sensitive signal processing components) overlap.

The separating portion may have a planar configuration. The separating portion may be configured to be detachably attachable to the at least one of first and second housing portion. At least one of the first and second housing portion may be open towards the separating portion.

The separating portion may comprise one or more parts. The one or more parts may be configured to be detachably attachable to each other. A first part of the separating portion may be configured to span the first and second separating region and to be detachably attachable to the first housing portion. A second part of the separating portion may be configured to span the first separating region and to be detachably attachable to the second housing.

In one variant, the separating portion may be an electromagnetic shielding portion. The electromagnetic shielding portion may in particular be configured to electromagnetically shield the first and the second PCB from each other. At least one of the separating portion and substantially the entire housing assembly may be made of metal, in particular of sheet metal. The sheet metal may be stainless steel.

The first housing portion and the second housing portion may be configured to substantially enclose the first PCB and the second PCB, respectively, in regions facing away from the separating portion. The first and the second PCB may each be configured to be detachably attachable to the separating portion. The first and the second PCB may each be configured to be spaced apart from the separating portion.

The separating portion may cover at least one of a) substantially the entire first housing portion at its side facing the second housing portion and b) substantially the entire second housing portion at its side facing the first housing portion.

The first housing portion may comprise one or more second convection openings spaced apart from the first convection openings so as to define a convection path from the one or more first convection openings over the first PCB to the one or more second convection openings. The one or more second convection openings may be outlet openings configured to allow an airflow from the interior of the first housing portion to the outside.

The housing assembly may comprise a hook configured to permit mounting the housing assembly in a hanging manner over ground. In a surgical tracking scenario, the hook may engage a structure on a patient support or operating room cart.

At least one of the one or more first convection openings may be arranged closer to ground than at least one of the one or more second convection openings. In particular, when the housing assembly is mounted via the hook. Further, if the first housing portion comprises multiple second convection openings (or multiple sets of such openings), the multiple second convection openings or opening sets may be arranged at different locations of the first housing portion so that regardless of the orientation of the housing assembly, the first one or more convection openings are located closer to ground than at least one of the multiple second convection openings or sets of such openings. One or more of the first and second convection openings may be arranged in an array.

The hook may be made of a heat-conductive material, in particular metal. The hook may be attached to one of the first housing portion and the second housing portion in a heat conducting manner so that the hook may be utilized as a heat sink and/or a heat conductor to a heat sink. The hook may comprise a plate-shaped end portion that may be attached in a spaced-apart relationship (and, optionally, in a heat-conducting manner) to one of the first housing portion and the second housing portion so as to define a convection channel between the hook and the respective housing portion.

In one variant, the housing assembly may comprise a housing shell enclosing the first housing portion, the second housing portion and the separating portion. The hook may be located outside the housing shell or may extend out of the housing shell. The housing shell may be made of a non-metallic material, in particular plastics. The housing shell may define a closed space devoid of any convection opening to an outside of the closed space. In this manner, dust or fluids are prevented from entering the housing shell. Moreover, the housing shell can easily be cleaned, which is particularly important in surgical use due to the need to maintain a sterile environment.

A first convection space may be delimited by the housing shell, the second housing portion and the first separating region. The one or more convection openings may communicate with the first convection space. A second convection space may be delimited by the housing shell and the first housing portion, wherein the one or more second convection openings communicate with the second convection space. The separating portion may comprise a third region that extends beyond the first housing portion and covers the second housing portion. In this case, the second convection space may be further delimited by the third separating region.

The housing assembly presented herein may be part of an electromagnetic tracking system. The electromagnetic tracking system may in particular be used for surgical purposes and, thus, may further comprise one or more surgical instruments with field sensors (e.g., coils) that can electrically be connected to one or both of the first PCB and the second PCB. The electromagnet tracking system may further comprise an electromagnetic field generator.

BRIEF DESCRIPTION OF THE DRAWINGS

Further features and advantages of the present disclosure will become apparent from the drawings and also from the following detailed description of exemplary embodiments. In the drawings:

FIG. 4A shows an isometric view of the housing assembly with an enclosing shell, including the front, bottom and right side of the housing assembly;

FIG. 4B shows a further isometric view of the housing assembly of FIG. 4A, including the back, bottom and left side of the housing assembly;

DETAILED DESCRIPTION

Figure 1A:
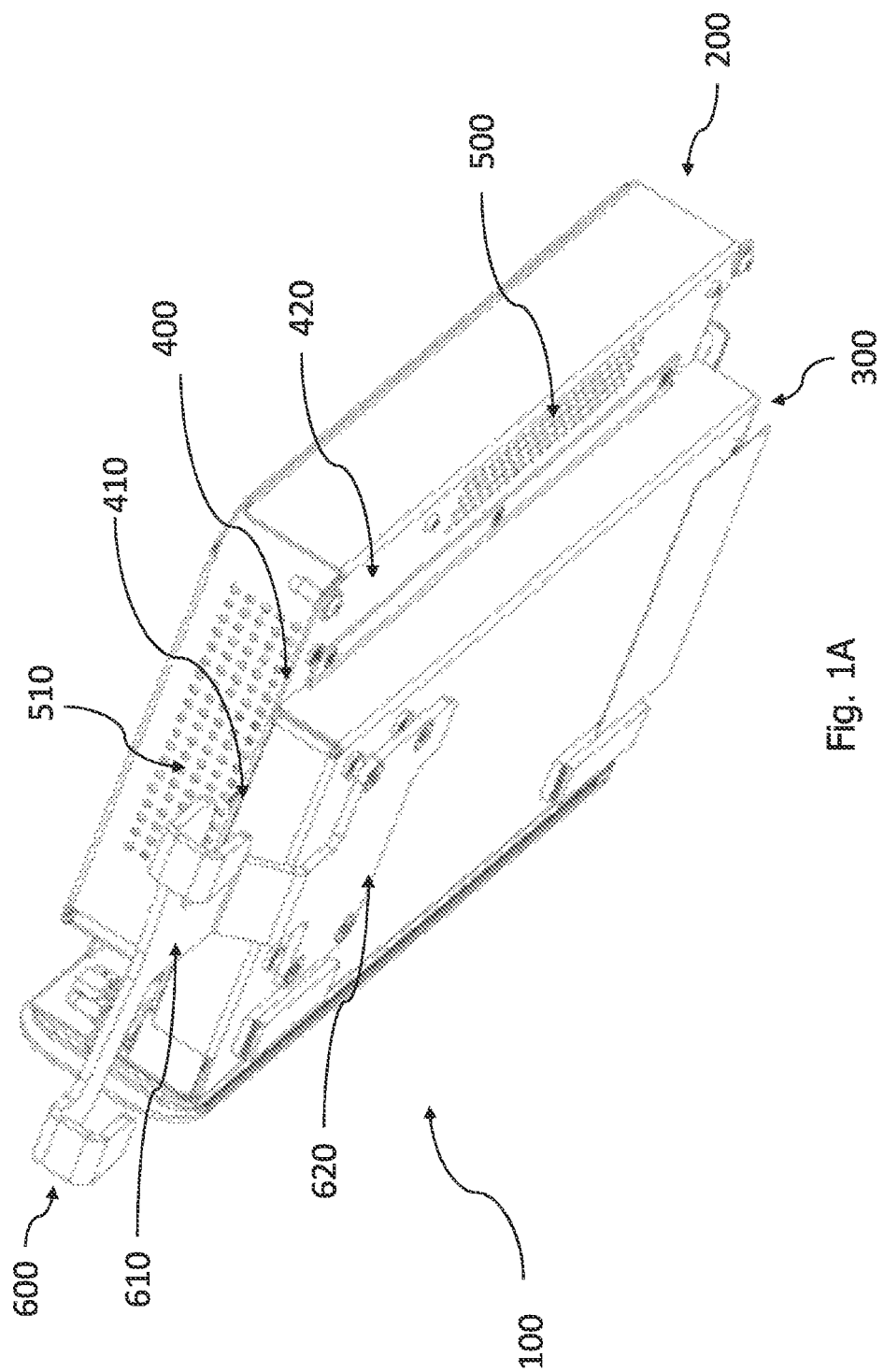
FIG. 1A shows a first isometric view of a housing assembly according to the present disclosure, including a back, a top and a left side of the housing assembly.

In this detailed description, the same reference numerals are used to denote identical or similar components and functions. In the following, housing assembly embodiments according to the present disclosure are described with references to FIGS. 1A to 5B.

FIG. 1A illustrates an isometric view of a housing assembly 100 according to the present disclosure. FIG. 1A shows the back side, top side and left side of the housing assembly 100. Those sides are defined from an operational perspective in which the housing assembly will be mounted in hanging manner (so that the top side is defined by the extension of a hook 600, as will be explained in greater detail below).

The housing assembly 100 comprises a first housing portion 200 configured to accommodate a first PCB (not visible in FIG. 1A, but described in detail with reference to FIGS. 2 and 3 below) and a second housing portion 300 configured to accommodate a second PCB 310 (not visible in FIG. 1A, but described in detail with reference to FIGS. 2 and 3 below). The first housing portion 200 and the second housing portion 300 are separated by a planar separating portion 400. The separating portion 400 has a substantially rectangular form. The separating portion 400 comprises a first region 410 in which the first housing portion 200 and the second housing portion 300 overlap. The separating portion 400 further comprises a second region 420 that extends beyond the second housing portion 300 and covers the first housing portion 200. The two housing portions 200, 300 and the separating portion 400 are made from sheet metal and, thus, shield electromagnetic fields.

In the view illustrated in FIG. 1A, the separating portion 400 thus forms a back side of the first housing portion 200 and a part of a front side of the second housing portion 300. The two housing portions 200, 300 thus are open towards, and closed by, the separating portion 400. The separating portion 400 has a third separating region (not visible in FIG. 1), that extends beyond the first housing portion 200 and covers the second housing portion 300 so that the separating portion 400 spans over the complete front side of the second housing portion 300.

In other realizations, the separating portion 400 may comprise multiple separating parts (not shown). For example, the separating portion 400 may comprise a first and a second planar part adjacent and detachably attachable to each other. The first planar part may span the first and second separating regions 410, 420 and may form the back side of the first housing portion 200. The second planar part may span the first separating region 410 and may form at least part of the front side of the second housing portion 300. Further, the separating portion 400 may have other forms than the substantially rectangular form shown in FIG. 1A, e.g., a curved or angled form. Moreover, it may also be non-planar and may, for example, have a stepped configuration.

Returning to the realization shown in FIG. 1A, the second separating region 420 forming a part of the back side of the first housing portion 200 comprises multiple first convection openings 500. In some realizations, the multiple first convection openings are located in an area of the second separation region 420 spanning a surface between 8 cm$^2$ and 1 cm$^2$, in particular between 5 cm$^2$ and 3 cm$^2$, for example 3.9 cm$^2$. The first housing portion 200 further comprises multiple second convection openings 510 located at a top side of the first housing portion 200. In some realizations, the multiple second convection openings are located in an area of the second separation region 420 spanning a surface between 5 cm$^2$ and 0.5 cm$^2$, in particular between 2.5 cm$^2$ and 1.5 cm$^2$, for example 2 cm$^2$. The multiple first convection openings 500 and the multiple second convection openings 510 are arranged to form a respective array of openings.

The multiple first convection openings 500 and the multiple second convection openings 510 define a convection path therebetween. In some realizations, this convection path stretches from the first convection openings 500 to the second convection openings 510. Additionally or alternatively to the second convection openings 510 located at the top side of the first housing portion 200, one or more other second convection openings 510 may be located at a different side of the first housing portion 200 (e.g., see FIG. 1C). In some realizations, the one or more other convection openings 510 are located in an area of the first housing portion 200 spanning a surface between 10 cm$^2$ and 1 cm$^2$, in particular between 7 cm$^2$ and 3 cm$^2$, for example 4.6 cm$^2$. In some realizations, such one or more other second convection openings 510 are located in the first housing portion 200 in such a way that regardless of the orientation of the housing assembly 100, at least one second convection opening is located further from ground than the one or more first convection openings 500. In such realizations, the first convection openings 510 may act as inlet openings for ambient air, and one or more of the second convection openings 510 act as outlet openings for air heated due to heat generated by electrical components of the first PCB 210.

As mentioned above, the housing assembly 100 further comprises a hook 600. The hook 600 comprises a first end portion 610 with a section upwardly extending away from a top side of the housing assembly 100. The first end portion 610 of the hook 600 comprises two U-shaped sections spaced apart from the top side of the housing assembly 100 and configured to permit mounting of the housing assembly 100 in a hanging manner over ground. In other realizations, the first end portion 610 of the hook 600 may be shaped differently, e.g. forming only one, or more than two, U-shaped portions or forming a V-shaped or any other shaped portion that permits mounting of the housing assembly 100 in a hanging manner over ground.

The hook 600 further comprises a second end portion 620 that is detachably fastened to the second housing portion 300. In other realizations, the second end portion 620 of the hook 600 may be fastened in a non-detachable manner to the second housing portion 300. In still further realizations, the second end portion 620 of the hook 600 may be fastened to the first housing portion 200 or to the first and the second housing portion 200, 300. In the present realization, the hook 600, the fastening elements 630 used to fasten the second end portion 620 of the hook 600 to the second housing portion 300, and the first and second housing portions 200, 300 are made of metal, i.e., of a heat conducting material. Thus, the hook 600 is configured to act as a heat sink or a heat conductor to transfer excess heat away from the first and the second housing portion 200, 300.

Figure 1B:
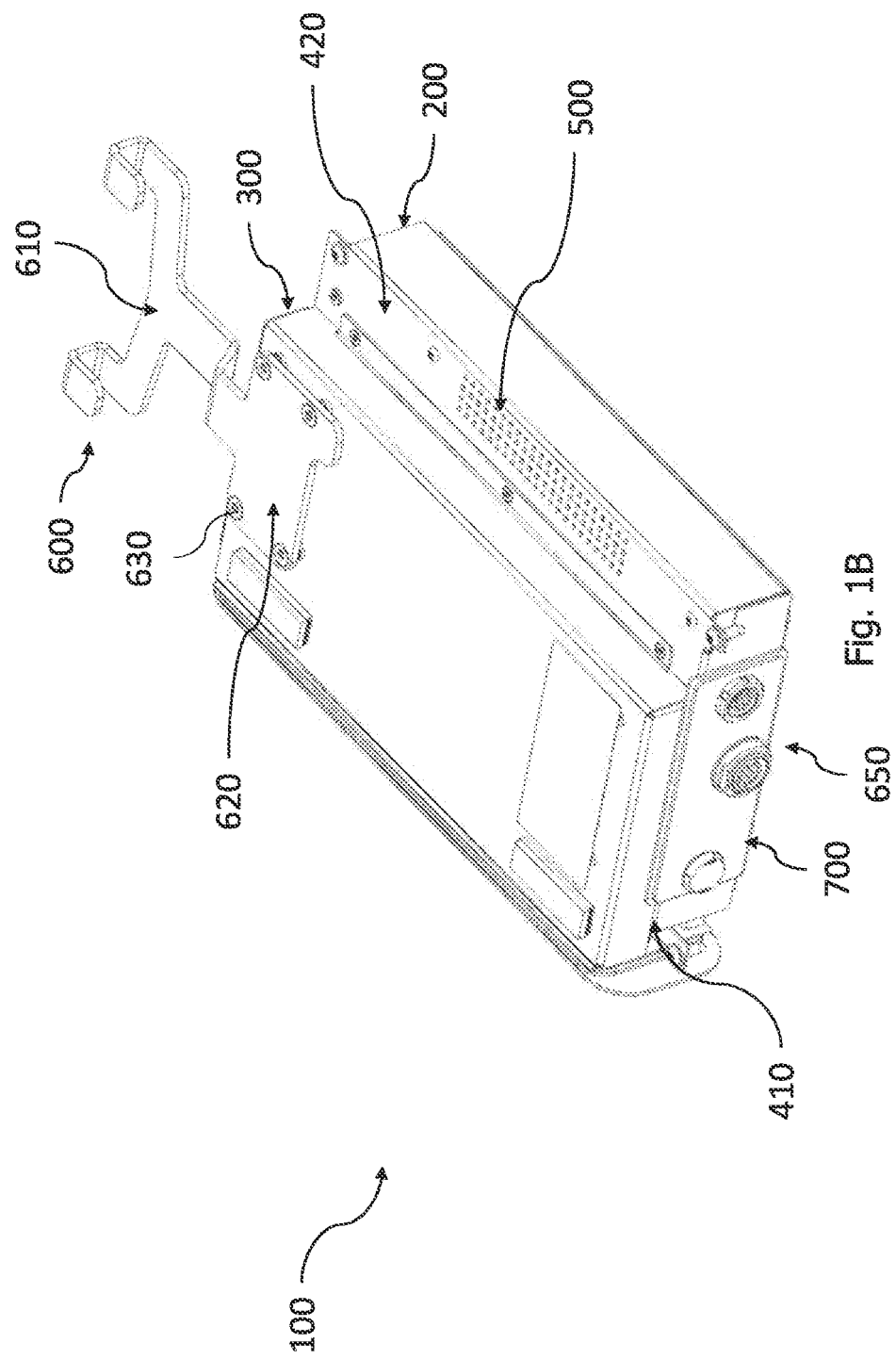
FIG. 1B shows another isometric view of the housing assembly, including the back, a bottom and the left side of the housing assembly.

FIG. 1B illustrates a further isometric view of the housing assembly 100 of FIG. 1A, showing the back, bottom and left side of the housing assembly 100. As illustrated in FIG. 1B, the first housing portion 200 comprises a bottom side with apertures for accommodating electric ports 650 comprised by the first PCB 210. A faceplate 700 with corresponding apertures is attached to the bottom side of the first housing portion 200. The number of apertures may be adapted depending on the electric ports 650 comprised by the first PCB 210. The ports 650 may serve for data communication with and power supply of one or more PCBs accommodated in one or both of the first and second housing portions 200, 300. Moreover, at least one of the ports 650 may be configured to be coupled to an external field generator (not shown).

Figure 1C:
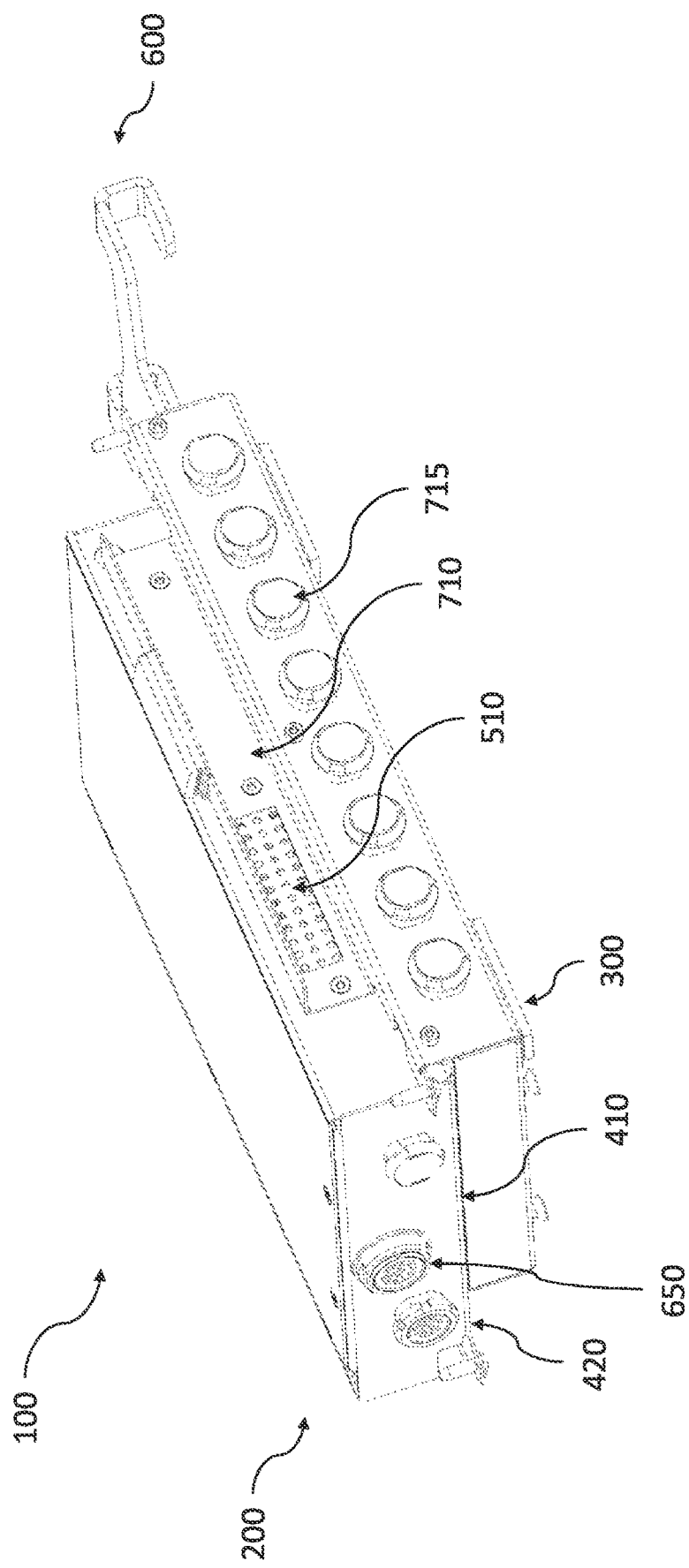
FIG. 1C shows a still further of an isometric view of the housing assembly, including a front, the bottom and a right side of the housing assembly.

FIG. 1C shows another isometric view of the housing assembly 100, including the front, bottom and right side of the housing assembly 100. As can be gathered from FIG. 1C, a set of further second convection openings 510 are located on the right side of the first housing portion 200. An attachment member 710, that is part of the second housing portion 300, is detachably attached to the right side of the first housing portion 200 and has an opening in a region of the further second convection openings 510. The set of second convection openings 510 located on the right side of the first housing portion 200 is provided in addition to the set of second convection openings 510 located on the top side of the first housing portion 200 (see FIG. 1). In some variants, one of those sets of second convection openings 510 may be omitted, or a third set of second convection openings may be provided at a different region (e.g., a different side) of the first housing portion 200.

Still referring to FIG. 1C, the second housing portion 300 comprises on its right side multiple apertures configured for accommodating electric ports 715 comprised by the second PCB 310 (not shown). The number and form of the apertures may be adapted based on the number and form of the electric ports 715 comprised by the second PCB 310. For example, there could be one or more apertures and/or the apertures could have a circular, rectangular or generally polygonal form.

Figure 1D:
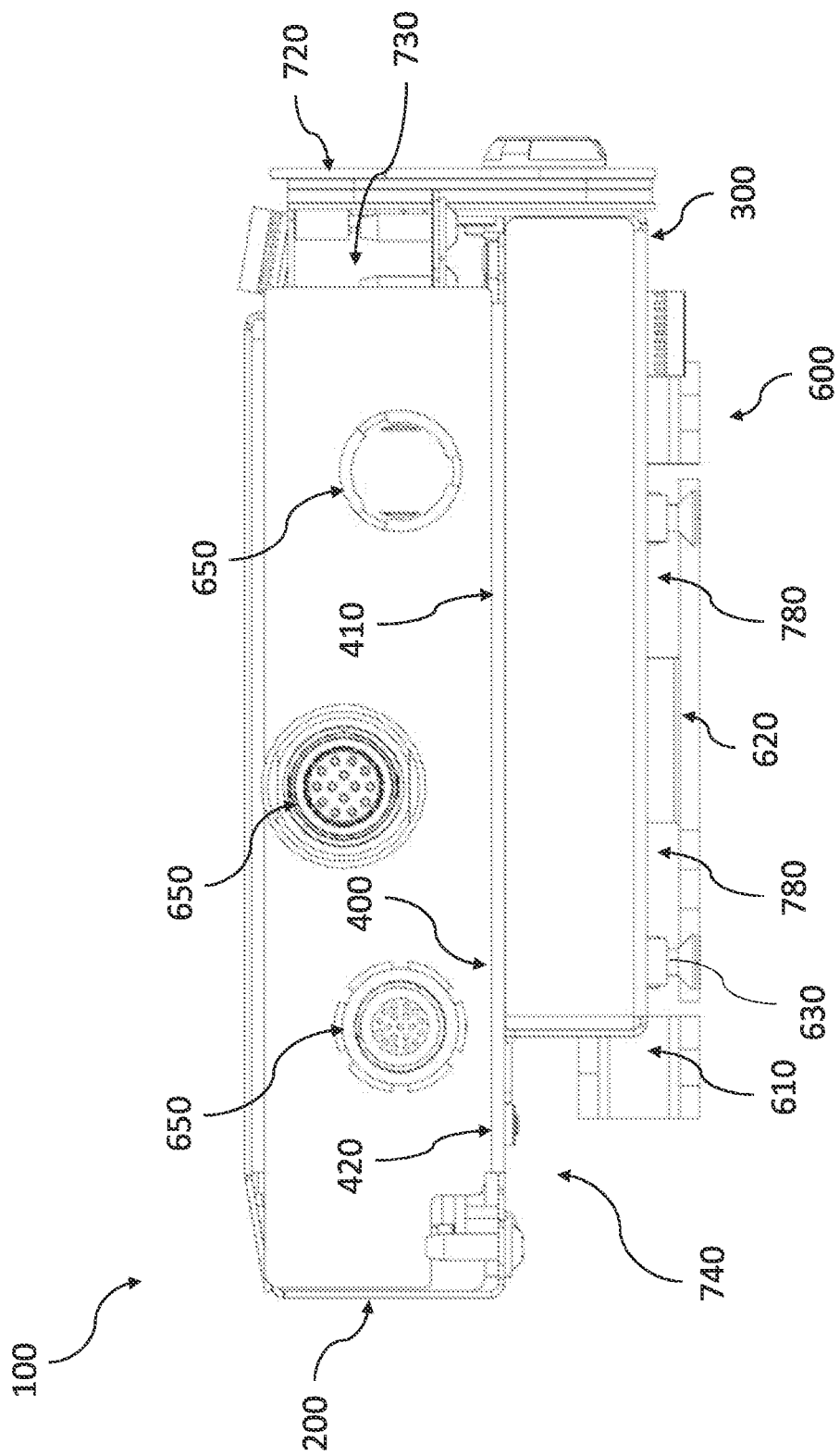
FIG. 1D shows a bottom view of the housing assembly.

FIG. 1D shows a bottom view of the housing assembly 100 of FIG. 1A. A multi-layer faceplate 720 is attached to the right side of the second housing portion 300. The faceplate 720 comprises multiple apertures corresponding to the apertures in the right side of the second housing portion 300 (as shown in FIG. 1C). The faceplate 720, a region of the separating portion and the right side of the first housing portion 200 (as well as a housing shell not shown in FIG. 1D) delimit a first convection space 730. The first convection space 730 is configured to allow an airflow within the convection space 510. Thus, a build-up of warm air immediately in front of the second convection openings 510 located on the right side of the first housing portion 200 is prevented. In some realizations, the first convection space 730 has a volume between 160 cm$^3$ and 40 cm$^3$, in particular between 100 cm$^3$ and 60 cm$^3$, for example, 83 cm$^3$. Similarly, a second convection space 740 is delimited by the left side of the second housing portion 300 and the second separating region 420 of the separating portion 400 (as well as the housing shell not shown in FIG. 1D). In some realizations, the second convection space 740 has a volume between 500 cm$^3$ and 120 cm$^3$, in particular between 300 cm$^3$ and 180 cm$^3$, for example, 238 cm$^3$. The first convection openings 500 allow an airflow from the second convection space 740 into the interior of the first housing portion 200. As such, non-heated ambient air can flow from the convection space 740 through the first convection openings 500 into the first housing portion 200 across a PCB accommodated in the first housing portion 200 and leave the first housing portion through the second convection openings 510 into the convection space 730.

As can also be gathered from FIG. 1D, the hook 600 is attached to the second housing part 300 in a spaced apart relationship. The hook 600 and the back side of the second housing portion 300 thus define a convection channel 780 allowing an airflow between the hook 600 and the second housing portion 300. As said, the first and the second housing portions 200, 300, the separating portion 400, the hook 600 and the fastening elements 630 are made of metal, so that the latter act as heat conductors for conducting heat from the second housing portion 300 to the hook 600.

Figure 2:
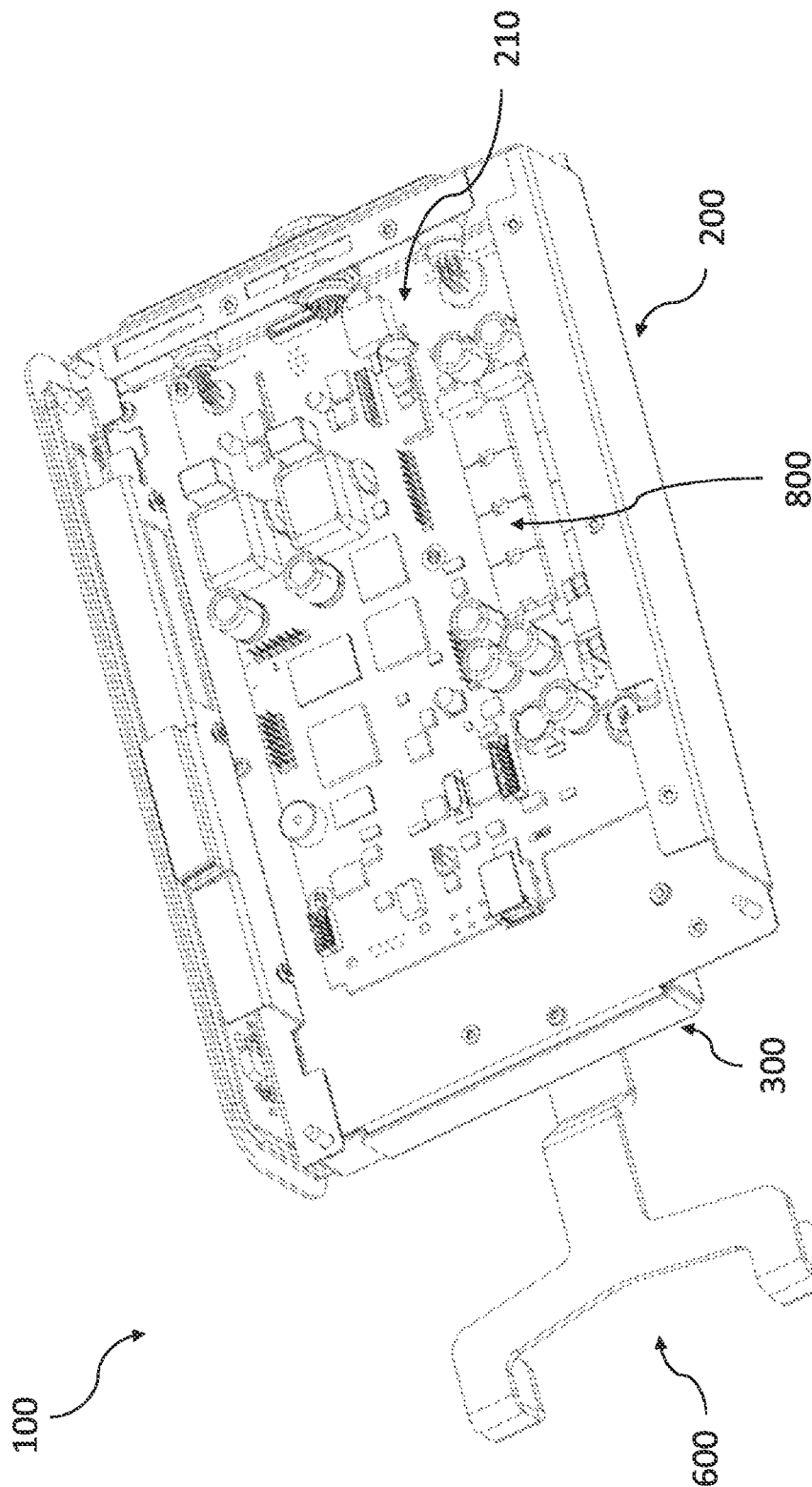
FIG. 2 shows a first PCB mounted to a separating portion of the housing assembly.

FIG. 2 shows an isometric view of the housing assembly 100 with, inter alia, a front wall being removed from the first housing portion 200. As such, a first PCB 210 accommodated in the first housing portion 200 becomes visible.

The first PCB 210 is mounted via spacers (not shown) to the separating portion 400 and comprises multiple electrical components generating high amounts of heat when operated, such as an array of drivers 800 for controlling an external electromagnetic field generator coupled to the drivers 800 via one of the ports 650. The drivers 800, in operation, also themselves generate electromagnetic fields possibly causing interference from the perspective of electrical components accommodated in the second housing portion 300, which will be mitigated by electromagnetic shielding properties of the separating portion 400 and the fact that an area of the first PCB 210 where the drivers 800 are located is offset from the second housing portion 300 by an amount substantially defined by the second separating region 420 (see FIG. 1A).

In some realizations, the drivers 800 are performance modules configured for powering an external electromagnetic field generator. In such realizations, the first PCB 210 may additionally comprises electronic components for controlling the drivers 800, and possibly electronic components for communicating with a host computer, e.g., per wired or wireless communication. In some realizations, the first PCB 210 may comprise signal processing components configured for calculating, or assisting the calculation of, the positions and orientations of external electromagnetic field sensors within an electromagnetic field generated by the external electromagnetic field generator.

The drivers 800 are located in an area of the first PCB 210 immediately adjacent to the first convection openings 500 in the second separating region 420 (see FIG. 1A).

The heat generated by the drivers 800 will initially heat the air adjacent to the drivers 800. Since the first convection openings 500 are located closer to ground than at least some of the second convection openings 510 (see FIGS. 1A and 1C), the heated air rises to and exits the first housing portion 200 through those second convection openings 510. Further, the heated air is replaced with non-heated air (i.e., ambient air) entering the first housing portion 200 through the first convection openings 500. As a result, an airflow from the first convection openings 500 over the drivers 800 (and possibly other electronic components) mounted on the first PCB 210 to the second convection openings 510 is established during operation.

Figure 3:
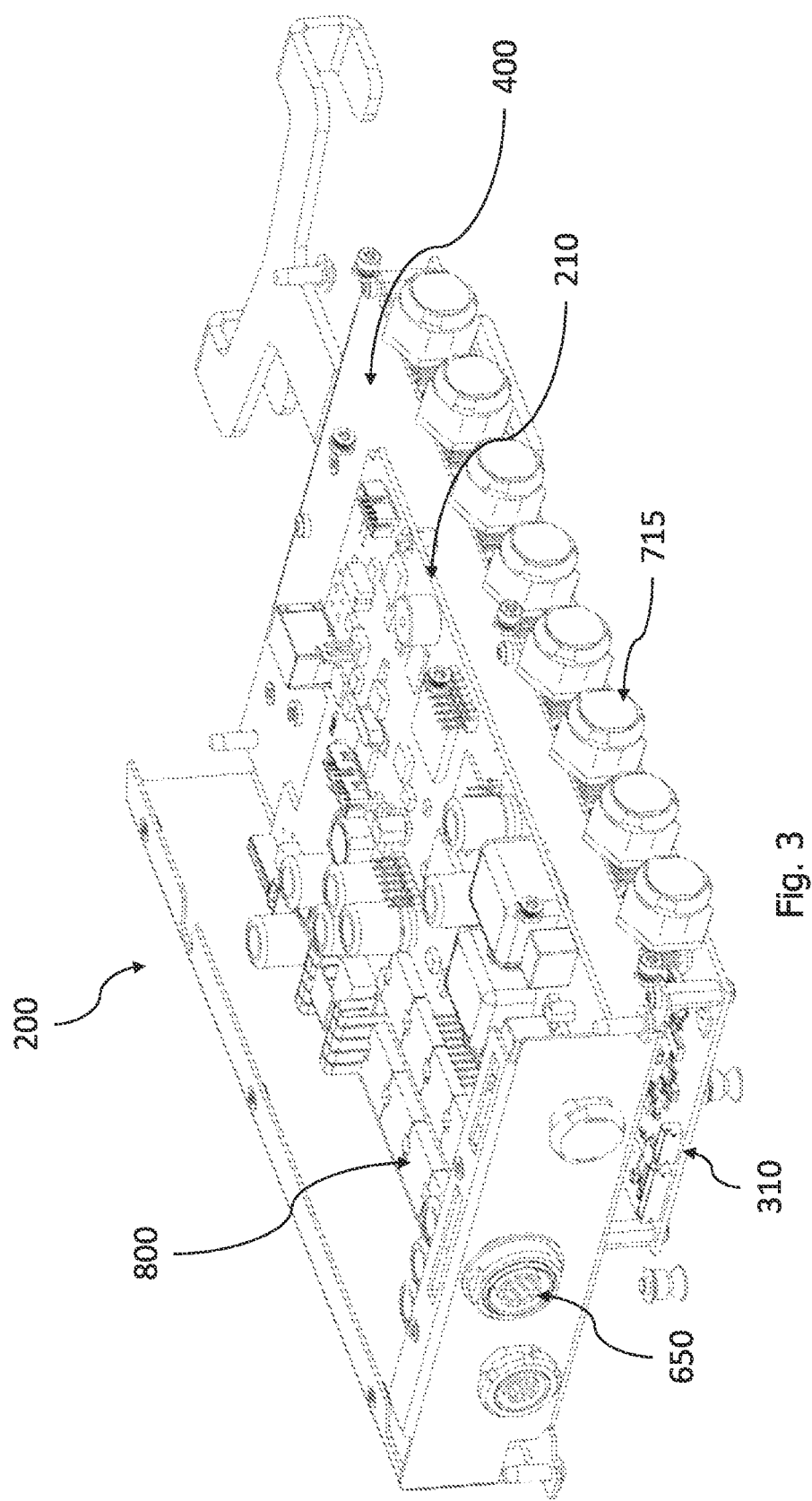
FIG. 3 shows a first PCB and a second PCB mounted to the separating portion of the housing assembly.

FIG. 3 shows an isometric view of the housing assembly 100 with, inter alia, the front wall being removed from the first housing portion 200 and the second housing portion being removed. FIG. 3 illustrates the first PCB 210 and a second PCB 310 both being mounted in a spaced-apart manner to the separating portion 400 of the housing assembly 100. The second PCB 310 comprises one or more electric ports 715 configured to be coupled to one or more external electromagnetic field sensors (e.g., coils located in surgical instruments) and one or more signal processing components configured to process sensor signals generated by the electromagnetic field sensors. In some realizations, the signal processing components of the second PCB 310 are configured for converting analogue signals received from the external electromagnetic field sensors to digital signals. The second PCB 310 may further be configured for transmitting the resulting digital signals to signal processing components of the first PCB 210. The first PCB 210 may then calculate, or assist the calculation of, the positions and orientations of the external electromagnetic field sensors.

In operation, electrical components of the first PCB 210, in particular the drivers 800, (and electrical components of the second PCB 310) will generate electromagnetic fields that cause interference with electrical components of the respective other PCB 210, 310. Further interference may be caused by the electromagnetic field generator that, during a surgical intervention with electromagnetic tracking assistance, will be located in the vicinity of the first and second PCBs 210, 230.

The interference may in particular falsify the signal processing of the signal processing components of the second PCB 310. To prevent or at least reduce such interference between the PCBs 210, 310, the separating portion 400 is configured as an electromagnetic shielding portion by being made of sheet metal (e.g., stainless steel). For the same reason, also the first housing portion 200 and the second housing portion 300 are made of sheet metal (e.g., stainless steel).

FIGS. 4A and 4B show schematic representations of an isometric view a housing shell 900 enclosing the housing assembly 100.

The housing shell 900 comprises a front portion 910 and a back portion 920. The front portion 910 and the back portion 920 are configured to be detachably attachable to one another so as to accommodate the housing assembly 100 therebetween. The housing shell 900 is further configured to accommodate the faceplate 720 so that the faceplate 720 forms at least a part of the right side of the housing shell 900, when the front portion 910 and the back portion 920 are attached to one another. The left side of the housing shell 900 is closed by sidewalls of the front portion 910 and the back portion 920. In the present realization, the housing shell 900 defines a closed space substantially devoid of any convection openings to an outside of the closed space. As such, the housing shell 900 can easily be cleaned and prevents dust and fluids from entering its interior. The housing shell 900 may be made of a non-metallic material, in particular plastics for safe and easy handling of the housing assembly by a user.

The hook 600 is located outside the housing shell 900 (see FIG. 4B). In more detail, the plate-shaped second end portion 620 of the hook 600 is arranged to fit into an opening in the back portion 920 of the housing shell 900 and close that opening (see FIG. 4B). In other embodiments, the second end portion 620 of the hook 600 may be located within the housing shell 900 and the hook 600, in particular its first end portion 610, extends to the outside of the housing shell 900.

Figure 5A:
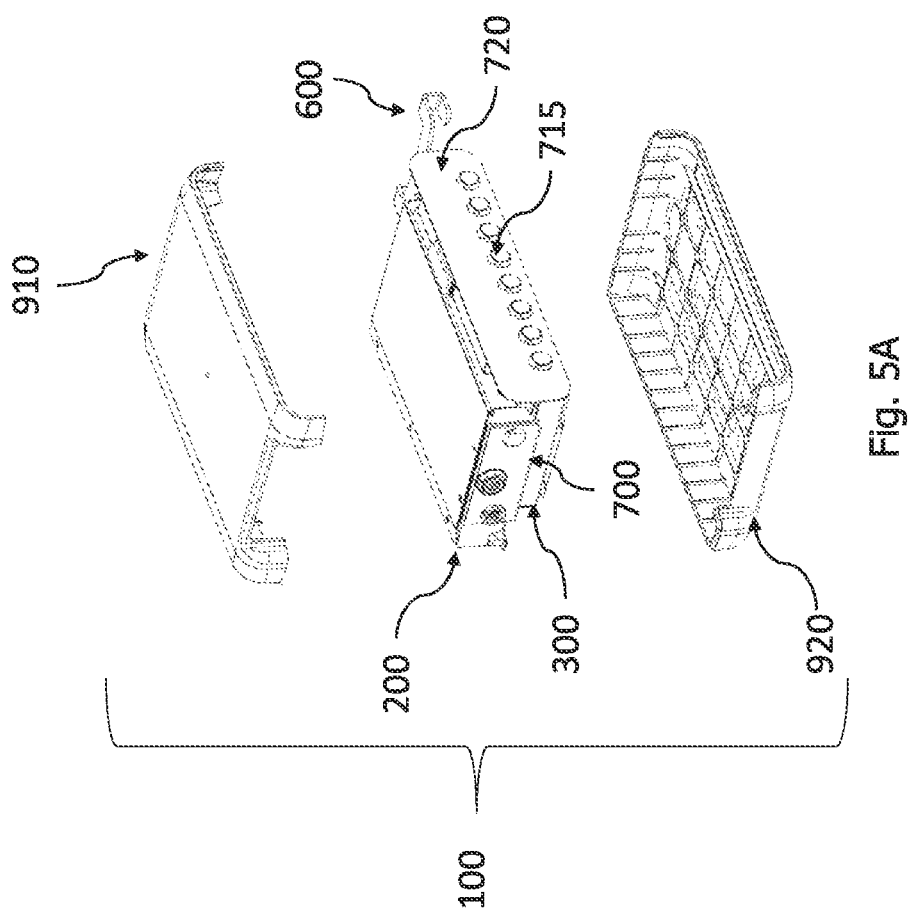
FIG. 5A shows an exploded view of the housing assembly of FIG. 4A.

In FIG. 5A, the housing assembly 100 with the housing shell 900 is shown in an exploded view. The housing shell 900 is configured to accommodate the first housing portion 200 and the second housing portion 300. The faceplate 720 is attached to the second housing portion 300.

Figure 5B:
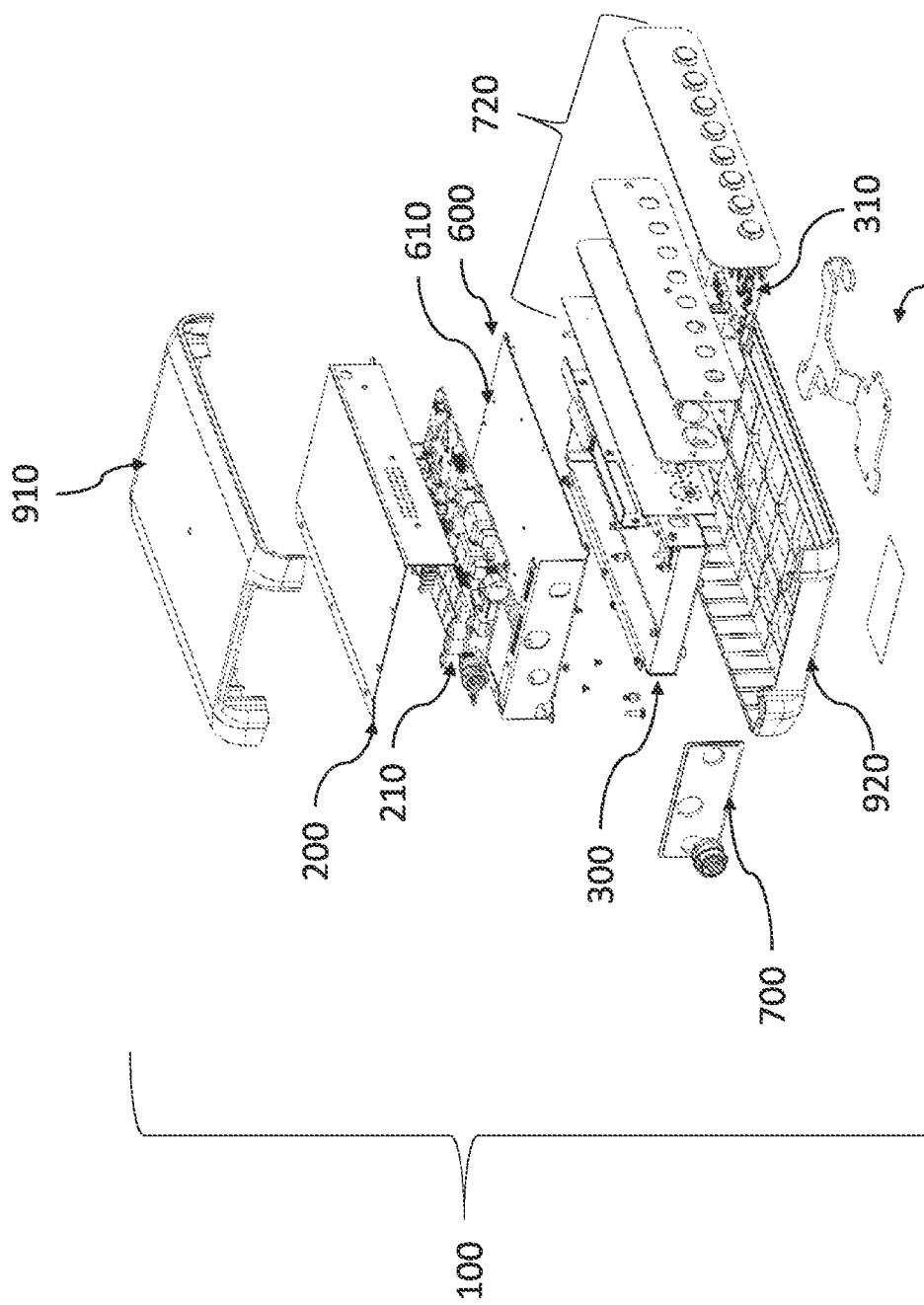
FIG. 5B shows a more detailed exploded view of the housing assembly of FIG. 4A.

FIG. 5B shows the housing assembly 100 in a more detailed exploded view. As may be gathered from FIG. 5B, the faceplate 720 attached to the right side of the second housing portion 300 comprises multiple layers. At least one of the multiple layers is made of electrically insulating material. The number of layers may be two or more, e.g., four layers, as shown in FIG. 5B. In some realizations, the faceplate 720 comprises up to four layers and the first layer (the layer closest to the second PCB 310) is a PCB comprising multiple LEDs (not shown) located around each aperture of the faceplate 720. A group of LEDs (e.g., arranged as a ring) may be associated with each aperture. The number of LEDs per LED group may be between 4 and 20, in particular between 8 and 16, for example 12. In some realizations, the LEDs are configured to emit light in different colours, for example, half of the LEDs may be configured to emit green light and the other half to emit orange light. The LEDs emitting light of different colours may be arranged in an alternating pattern around the respective aperture. The second layer is optional and may be a plastic layer, in particular a frosted plastic layer, comprising circular perforations around each LED group. The third layer is likewise optional and may be a diffusion layer configured for generating an effect of a continuous light circle around an aperture. The fourth layer is also optional and may by a partially transparent layer. The fourth layer may be designed to comprise print artwork for identifying the respective electrical ports of the second PCB 310 associated with the respective apertures of the faceplate 720 (e.g., using a consecutive numbering).

As has become apparent from the above detailed description, the housing approach presented herein solves a plurality of problems, which in some cases are linked. A compact housing design for accommodating multiple PCBs is provided that simultaneously provides for an advanced heat management and efficient electromagnetic shielding properties, while being easy to clean in a surgical environment.

The invention claimed is:

1. A housing assembly for accommodating printed circuit boards, PCBs, the housing assembly comprising:
A housing assembly for accommodating printed circuit boards (PCBs),
a second housing portion configured to accommodate a second PCB; and
a separating portion separating the first housing portion from the second housing portion, wherein the separating portion comprises:
a first region in which the first housing portion and the second housing portion overlap; and
a second region that extends beyond the second housing portion and covers the first housing portion, wherein the second separating region comprises one or more first convection openings.

2. The housing assembly of claim 1, further comprising the first PCB, wherein the first PCB comprises one or more heat-generating electrical components, and wherein the first PCB is accommodated in the first housing portion with the one or more heat-generating electrical components being located adjacent to the first convection openings.

3. The housing assembly of claim 2, further comprising the second PCB, wherein the second PCB comprises:
one or more electric ports configured to be coupled to one or more external electromagnetic field sensors; and
one or more signal processing components configured to process sensor signals generated by the one or more electromagnetic field sensors,
wherein the one or more heat-generating electrical components are drivers for controlling an external electromagnetic field generator that generates an electrical field to be measured by the one or more electromagnetic field sensors.

4. The housing assembly of claim 1, further comprising the second PCB, wherein the second PCB comprises:
one or more electric ports configured to be coupled to one or more external electromagnetic field sensors; and
one or more signal processing components configured to process sensor signals generated by the one or more electromagnetic field sensors.

5. The housing assembly of claim 1, wherein at least one of (a) the separating portion has a planar configuration, (b) the separating portion is an electromagnetic shielding portion, and (c) at least one of the separating portion and substantially the entire housing assembly is made of metal.

6. The housing assembly of claim 1, wherein the first housing portion and the second housing portion are configured to substantially enclose the first PCB and the second PCB, respectively, in regions facing away from the separating portion.

7. The housing assembly of claim 1, wherein the separating portion covers at least one of (a) substantially the entire first housing portion at its side facing the second housing portion, and (b) substantially the entire second housing portion at its side facing the first housing portion.

8. The housing assembly of claim 1, wherein the first housing portion comprises one or more second convection openings spaced apart from the first convection openings so as to define a convection path from the one or more first convection openings over the first PCB to the one or more second convection openings.

9. The housing assembly of claim 8, further comprising a hook configured to permit mounting the housing assembly in a hanging manner over ground, wherein at least one of the one or more first convection openings is arranged closer to the ground than at least one of the one or more second convection openings.

10. The housing assembly of claim 1, further comprising a hook configured to permit mounting the housing assembly in a hanging manner over ground.

11. The housing assembly of claim 10, wherein the hook is made of a heat-conductive material.

12. The housing assembly of claim 10, wherein the hook comprises a plate-shaped end portion that is attached in a spaced-apart relationship to one of the first housing portion and the second housing portion so as to define a convection space between the hook and the respective housing portion.

13. The housing assembly of claim 10, further comprising a housing shell enclosing the first housing portion, the second housing portion, and the separating portion, wherein the hook is located outside the housing shell or extends out of the housing shell.

14. The housing assembly of claim 1, further comprising a housing shell enclosing the first housing portion, the second housing portion, and the separating portion.

15. The housing assembly of claim 14, wherein at least one of (a) the housing shell is made of a non-metallic material, and (b) the housing shell defines a closed space devoid of any convection opening to an outside of the closed space.

16. The housing assembly of claim 14, wherein the first housing portion comprises one or more second convection openings spaced apart from the first convection openings so as to define a convection path from the one or more first convection openings over the first PCB to the one or more second convection openings, wherein a first convection space is delimited by the housing shell and the first housing portion, and wherein the one or more second convection openings communicate with the first convection space.

17. The housing assembly of claim 14, wherein a second convection space is delimited by the housing shell, the second housing portion, and the second separating region, and wherein the one or more first convection openings communicate with the second convection space.

18. The housing assembly of claim 17, wherein the separating portion comprises a third separating region that extends beyond the first housing portion and covers the second housing portion the second convection space is further delimited by the third separating region.

19. The housing assembly of claim 1, wherein the separating portion comprises a third separating region that extends beyond the first housing portion and covers the second housing portion.

20. An electromagnetic tracking system comprising:
one or more electromagnetic field sensors;
a housing assembly for accommodating printed circuit boards (PCBs), the housing assembly comprising:
 a first housing portion configured to accommodate a first PCB;
 a second housing portion configured to accommodate a second PCB; and
 a separating portion separating the first housing portion from the second housing portion, wherein the separating portion comprises:
 a first region in which the first housing portion and the second housing portion overlap;
 a second region that extends beyond the second housing portion and covers the first housing portion, wherein the second separating region comprises one or more first convection openings;
a first PCB accommodated in the first housing portion; and
a second PCB accommodated in the second housing portion, wherein one of the first and second PCBs is configured to process sensor signals generated by the one or more electromagnetic field sensors.

* * * * *

UNITED STATES PATENT AND TRADEMARK OFFICE
CERTIFICATE OF CORRECTION

PATENT NO. : 12,078,691 B2
APPLICATION NO. : 17/903395
DATED : September 3, 2024
INVENTOR(S) : Melder et al.

Page 1 of 1

It is certified that error appears in the above-identified patent and that said Letters Patent is hereby corrected as shown below:

In the Claims

In Column 10, Line 21-24 Claim 1:
Please replace:
"A housing assembly for accommodating printed circuit boards, PCBs, the housing assembly comprising:
A housing assembly for accommodating printed circuit boards (PCBs),"

With:
-- "A housing assembly for accommodating printed circuit boards (PCBs), the housing assembly comprising:
    a first housing portion configured to accommodate a first PCB;" --

Signed and Sealed this
Twenty-first Day of January, 2025

Coke Morgan Stewart
*Acting Director of the United States Patent and Trademark Office*